US009101924B2

(12) United States Patent
Ye et al.

(10) Patent No.: US 9,101,924 B2
(45) Date of Patent: Aug. 11, 2015

(54) INTERFACE DEVICE FOR BIO-CHIP

(75) Inventors: Jiaming Ye, Beijing (CN); Pinhong Wang, Beijing (CN); Guoqing Wang, Beijing (CN); Wanli Xing, Beijing (CN)

(73) Assignees: CAPITALBIO CORPORATION, Beijing (CN); TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 14/006,512

(22) PCT Filed: Feb. 10, 2012

(86) PCT No.: PCT/CN2012/070998

§ 371 (c)(1),
(2), (4) Date: Sep. 20, 2013

(87) PCT Pub. No.: WO2012/126292

PCT Pub. Date: Sep. 27, 2012

(65) Prior Publication Data

US 2014/0010733 A1 Jan. 9, 2014

(30) Foreign Application Priority Data

Mar. 22, 2011 (CN) .......................... 2011 1 0068678

(51) Int. Cl.
*G01N 15/06* (2006.01)
*G01N 33/00* (2006.01)
(Continued)

(52) U.S. Cl.
CPC ........... *B01L 3/502* (2013.01); *B01L 3/502715* (2013.01); *B01L 3/502784* (2013.01); *B01L 2200/0689* (2013.01); *B01L 2200/141* (2013.01); *B01L 2300/0816* (2013.01);
(Continued)

(58) Field of Classification Search
USPC .......... 422/50, 68.1, 544, 545, 546, 502, 503, 422/504; 436/43
See application file for complete search history.

(56) References Cited

U.S. PATENT DOCUMENTS

| | | | | |
|---|---|---|---|---|
| 7,097,809 | B2 * | 8/2006 | Van Dam et al. | 422/502 |
| 7,351,303 | B2 * | 4/2008 | Liu et al. | 156/297 |

(Continued)

FOREIGN PATENT DOCUMENTS

| | | |
|---|---|---|
| CN | 1568427 | 1/2005 |
| CN | 2702313 | 5/2005 |
| CN | 1683561 | 10/2005 |
| CN | 1905835 | 1/2007 |

(Continued)

OTHER PUBLICATIONS

International Search Report from International Application No. PCT/CN2012/070998 mailed May 17, 2012.

*Primary Examiner* — Brian J Sines
(74) *Attorney, Agent, or Firm* — Merchant & Gould P.C.

(57) ABSTRACT

An interface device for bio-chip at least comprises an interface unit, said interface unit consisting of instrument interface layer, fluid channel layer and sample interface layer. The instrument interface layer has at least one instrument interface. The fluid channel layer has one hollow-out fluid channel. The sample interface layer has at least one sample interface, and both ends of said fluid channel connect to the sample interface and the instrument interface respectively. The interface device separates sample solutions from the instrument interface by gas or liquid in the fluid channel, thus to avoid direct contacts between sample solutions and instrument interface which will cause pollution, and omitting cleaning processes after using instruments. With simple structure, easy operation and low cost, it applies to chemistry field, biology field and medical analysis field.

10 Claims, 3 Drawing Sheets

(51) Int. Cl.
*G01N 33/49* (2006.01)
*B01L 3/00* (2006.01)

(52) U.S. Cl.
CPC . *B01L 2300/0874* (2013.01); *B01L 2300/0887* (2013.01); *B01L 2400/0487* (2013.01)

(56) References Cited

U.S. PATENT DOCUMENTS

| | | | | |
|---|---|---|---|---|
| 7,544,506 | B2 * | 6/2009 | Breidford et al. .......... | 435/288.5 |
| 2002/0176802 | A1 | 11/2002 | Chung et al. | |

FOREIGN PATENT DOCUMENTS

| | | |
|---|---|---|
| CN | 1974751 | 6/2007 |
| CN | 101460953 | 6/2009 |
| CN | 101896599 | 11/2010 |
| CN | 102250751 | 11/2011 |
| TW | 200739075 | 10/2007 |
| WO | WO 03/015922 | 2/2003 |
| WO | WO 2006/018044 | 2/2006 |
| WO | WO 2006/088427 | 8/2006 |
| WO | WO 2008/039875 | 4/2008 |
| WO | WO 2010/019969 | 2/2010 |

* cited by examiner

INTERFACE DEVICE FOR BIO-CHIP

The present application is a National Stage Application of PCT/CN2012/070998, filed 10 Feb. 2012, which claims benefit of Chinese patent application No. 201110068678.x filed on 22 Mar. 2011 in The Patent Office of the People's Republic of China, and titled "Interface Device for Bio-Chip", which applications are incorporated herein by reference. To the extent appropriate, a claim of priority is made to each of the above disclosed applications.

FIELD OF INVENTION

The present invention relates to an interface device for bio-chip.

BACKGROUND OF THE INVENTION

Bio-chip is a multidisciplinary comprehensive technology that has been developed at the end of 20th century. As a technical platform, bio-chip has been extensively applied in many fields such as gene expression, functional genomics, disease diagnosis and drug screening etc., and has gradually extended to other areas including biosynthesis, biochemical reaction and nano-biology etc.

Large instruments are needed for the handling and treatment of bio-chips and samples, to avoid cross contamination among different samples. At present, most bio-chips are disposable, while the interfaces between the instrument and the chip are not. After the operation is completed for each chip, time-consuming procedures such as cleaning and disinfection are performed to the instrument and the chip, to avoid the contamination resulted from the residue of chemical or biological molecules at the interfaces. Although contamination can be alleviated to a certain degree by increasing the cleaning process, problems, such as tedious operation process, bulky cleaning reagent consumption and incomplete disinfection and so on, still bother the users, and more or less limit the popularization and application of the bio-chip technology.

SUMMARY OF THE INVENTION

The objective of the present invention is to provide an interface device for bio-chips with simple structure, convenient manipulation and low cost. The interface device for bio-chip separates sample solutions from the interface of an instrument, avoiding sample contamination due to direct contact between a plurality of sample solutions and the interface of an instrument.

The interface device for bio-chip provided herein comprises at least one interface unit formed by an instrument interface layer, a fluid channel layer and a sample interface layer sealed together. The instrument interface layer is provided with at least one instrument interface. The fluid channel layer is provided with a hollow-out fluid channel. The sample interface layer is provided with at least one sample interface. The two ends of the fluid channel are connected to the sample interface and the instrument interface, respectively.

The interface unit of the interface device for bio-chip provided herein can also be formed by an instrument interface layer and a sample interface layer sealed together. The instrument interface layer is provided with at least one instrument interface and a groove. The sample interface layer is provided with at least one sample interface. The groove serves as the fluid channel, with two ends connected to the sample interface and the instrument interface respectively.

The interface unit of the interface device for bio-chip provided herein can also be formed by an instrument interface layer and a sample interface layer sealed together. The instrument interface layer is provided with at least one instrument interface. The sample interface layer is provided with at least one sample interface and a groove. The groove serves as the fluid channel, with two ends connected to the sample interface and the instrument interface respectively.

The shape of the interface device for bio-chip provided herein can be plate or disc, or can be designed based on practical demands. Modifications or proper alterations can be made to the product described herein by a skilled person to implement and utilize the technique provided by the present invention. All similar alterations and modifications should be regarded to fall into the scope of the present invention.

In the interface device for bio-chip provided herein, the instrument interface layer, the fluid channel layer and the sample interface layer are made of materials independently selected from the group comprising glass, high molecular weight polymers, silicon wafer, metal or metal oxide, preferably polycarbonate, polypropylene, organic glass, polystyrene, ABS, polyethylene, polyvinyl chloride and polyformaldehyde.

In the interface device for bio-chip is provided herein, the instrument interface layer, the fluid channel layer and the sample interface layer can be sealed together through an adhesive, welding or a sealing element. When the layers are made of glass, high molecular polymers, silicon wafer, metal or metal oxide, the sealing is preferably implemented using an adhesive selected from the group comprising calendering adhesive, melt adhesive, reactive adhesive, solvent adhesive, emulsion adhesive or solventless liquid adhesive. When the layers are made of metal or metal oxide, sealing can also be implemented by welding.

In order to achieve simultaneous manipulation of a plurality of bio-chip samples and to avoid cross contamination among the samples, the number of the sample interfaces in the interface device for bio-chip provided herein is from 1 to 8, thereby not only avoiding the contact contamination between the sample and the instrument, but also avoiding the cross contamination among samples.

Preferably, an interface device for bio-chip is provided herein, in which the number of instrument interfaces is from 1 to 8.

The interface device for bio-chip provided herein can be a separate device, and can also be integrated into a bio-chip as a contamination preventive functional unit.

The interface device for bio-chip described herein can be used to prevent a static hybridization bio-chip from contamination. After adding a sample solution into the sample well of the bio-chip, the interface device described herein and the bio-chip are sealed together by adhesive or clamping using a mechanical clamp so that the sample interface of the interface device is in communication with the sample well of the bio-chip, and the instrument interface of the interface device is closed. After placing the interface device and the bio-chip into the hybridization box, static water bath or air bath hybridization is carried out, so that the contact contamination between the sample solution and the hybridization box can be avoided. As such, the cleaning of the hybridization box can be omitted, and a number of hybridization experiments can be repeated using the same hybridization box.

The interface device for bio-chip described herein can be further used to prevent the contamination of reciprocating flow hybridization bio-chip. A reciprocating flow dynamic hybridization bio-chip comprises a sample injection unit and a bio-chip, wherein the sample injection unit at least comprises one hybridization reaction chamber, two microfluid channels and two through holes. The sample injection unit is formed by sealing between a cover layer and a microfluid layer. The cover layer is provided with two through holes. The microfluid layer is provided with one hollow-out hybridization reaction chamber and two hollow-out microfluid channels, with each of said microfluid channels being connected to the hybridization reaction chamber at one end, and to a through hole of the cover layer at the other end. The microfluid layer of the sample injection unit is sealed with the bio-chip, and the hybridization reaction chamber is in communication with the bio-probe array zone of the bio-chip.

After adding sample solution into the through hole of the reciprocating flow hybridization bio-chip, the interface device described herein and the reciprocating flow hybridization bio-chip are sealed together by a lock ring, a sealing element or by clamping using a mechanical clamp, so that the sample interface of the interface device is in communication with a through hole of the bio-chip. The gas outlet of the pump valve system used to supply power for the reciprocating flow is in communication with the instrument interface of the interface device.

When the pump valve system used to supply gas pressure starts to work, it pushes the sample solution by positive pressure until the DNA sample reaches the hybridization reaction chamber. Thereafter, it draws the sample solution back by negative pressure. When moves back and forth in the hybridization reaction chamber, the sample solution flows from the reciprocating flow hybridization bio-chip in the lower layer to the fluid channel of the interface device in the upper layer through the sample interface. The fluid channel is designed to be long enough to make sure that the sample solution does not contact the instrument interface during the reciprocating flow, and thus the contamination due to the direct contact between the sample solution and the interface of the pump valve system can be avoided.

When used to prevent contamination of the reciprocating flow hybridization bio-chips, the interface device for bio-chip provided herein separates the sample solution from the instrument interface by the fluid inside the fluid channel, and thereby avoiding contamination to the instrument resulted from the direct contact between the sample solution and the instrument interface. The fluid in the fluid channel is a gas or liquid that does not diffuse into, dissolve in or react with the sample solution.

During operation of the interface device for bio-chip provided herein, the sample interface and the instrument interface are connected to corresponding sample well of a bio-chip or the instrument, and then it is sealed with the bio-chip by a sealing element such as a gasket and a lock ring etc. The gasket and the lock ring can be made of metal materials, and non-metal materials, such as rubber, plastics, ceramics, graphite etc, or composite materials, such as rubber-asbestos plate. Rubber elastomers are most widely used at present.

The advantages of the present invention are as follows: the use of the interface device for bio-chip described herein enables prevention of contamination of the instrument by the sample, abolish the need for tedious cleaning processes after operation. The device has the properties of simple structure, easy operation and low cost, and is suitable for various applications in the fields of chemistry, biology and medical analysis, and are promising in terms of economic value and social value.

(a) is a plane schematic diagram; (b) is a three-dimensional structural schematic diagram. 1 is the instrument interface of the interface device for bio-chip, 2 is the fluid channel, and 3 is the sample interface of the interface device for bio-chip.

Figure 2:
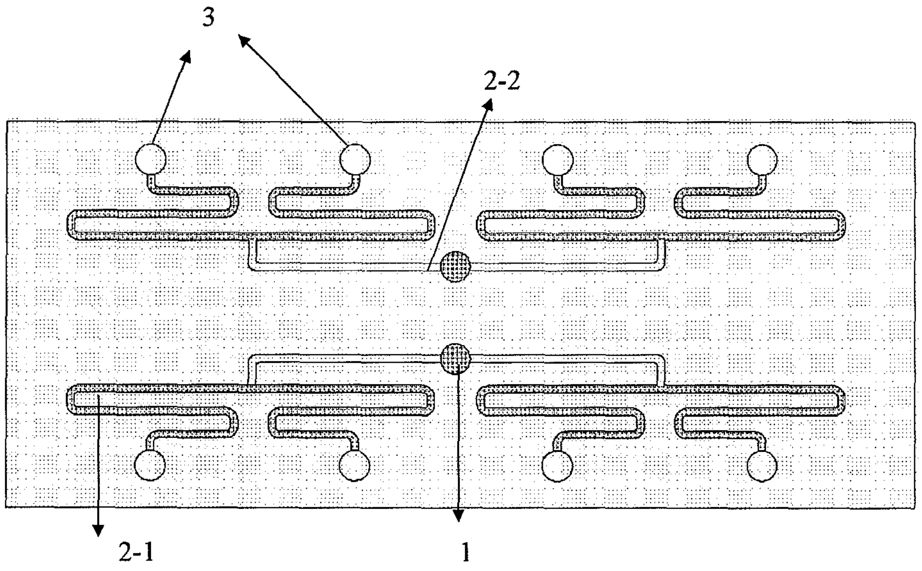

FIG. 2 is the schematic diagram showing the interface device that prevents the cross contamination among a plurality of samples and the contamination between the sample and the instrument interface. 1 is the instrument interface of the interface device for bio-chip; 3 is the sample interface of the interface device for bio-chip; 2-1 is the fluid channel used to prevent the contamination between the sample and the instrument interface; 2-2 is the fluid channel used to prevent the cross contamination among a plurality of different samples.

Figure 3:
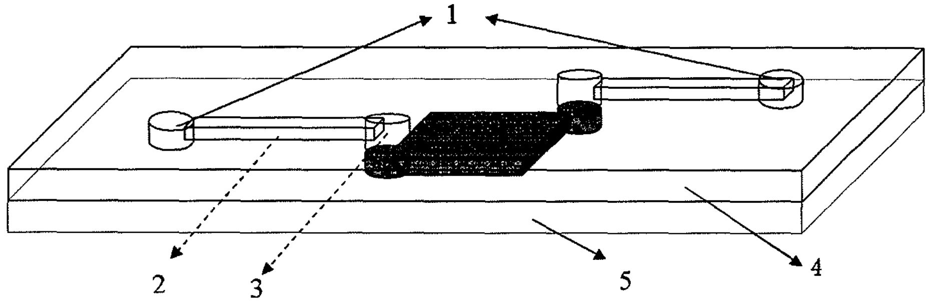

FIG. 3 is the schematic diagram showing the effect of the interface device for bio-chip described herein for preventing the contamination of a static hybridization bio-chip; wherein, 1 is the instrument interface of the interface device for bio-chip; 3 is the sample interface of the interface device for bio-chip; 4 is the interface device; 5 is the static hybridization bio-chip.

Figure 4:
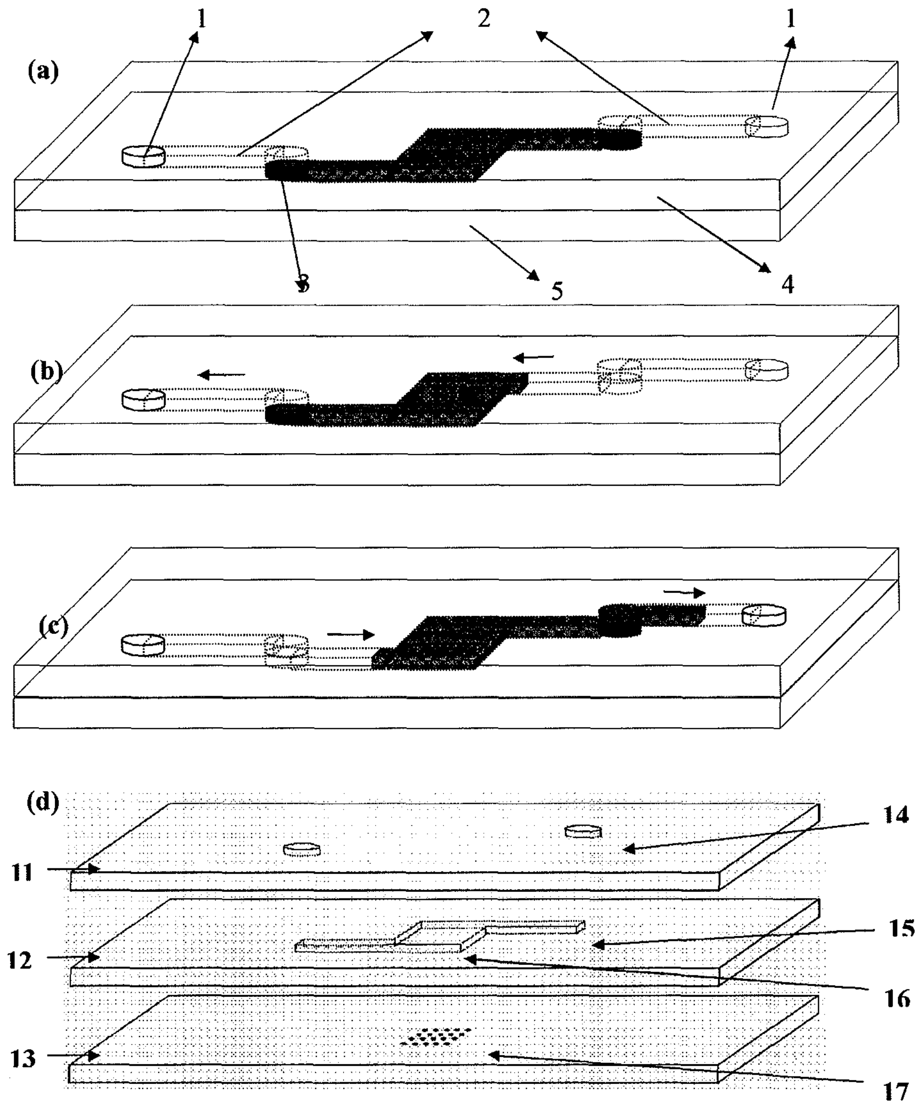

FIG. 4 is the schematic diagram showing the use process of the interface device described herein to prevent the contamination of the reversing flow hybridization bio-chip;

FIG. 4*a*: 1 is the instrument interface of the interface device for bio-chip; 2 is the fluid channel; 3 is the sample interface of the interface device for bio-chip; 4 is the interface device; 5 is the reversing flow hybridization bio-chip;

FIG. 4*b* and FIG. 4*c* show the reversing flow of the solution inside the fluid channel driven by gas pressure;

FIG. 4*d* is the structural schematic diagram for the reversing flow hybridization bio-chip, wherein 11 is the cover layer; 12 is the microfluid layer; 13 is the microarray chip, which can be a DNA chip or a protein chip, with a size of 25×75 mm; 14 is the through hole; 15 is the microfluid channel; 16 is the hybridization reaction chamber; 17 is the bio-probe array.

DESCRIPTION OF THE PREFERRED EMBODIMENTS

An interface device for bio-chip is disclosed by the present invention, which can be implemented through properly modifying the processing parameters by the one of skill in the art with reference to the content herein. Particularly, it should be noted that all similar alternatives and modifications are apparent to the one of skill in the art, all of which are regarded to be included in the present invention. The product according to the present invention and the application thereof have been described by preferable working examples, and it is apparent that modification, appropriate change and the combination thereof can be made to the method and the application described herein by those skilled in the art, without departing from the content, spirit and scope of the invention, in order to achieve and apply the techniques disclosed in the present invention.

The present invention will be further explained with reference to the specific examples as below, in order to make the technical proposal of the present invention better understood by one of ordinary skill in the art.

EXAMPLES

Example 1

Figure 1:
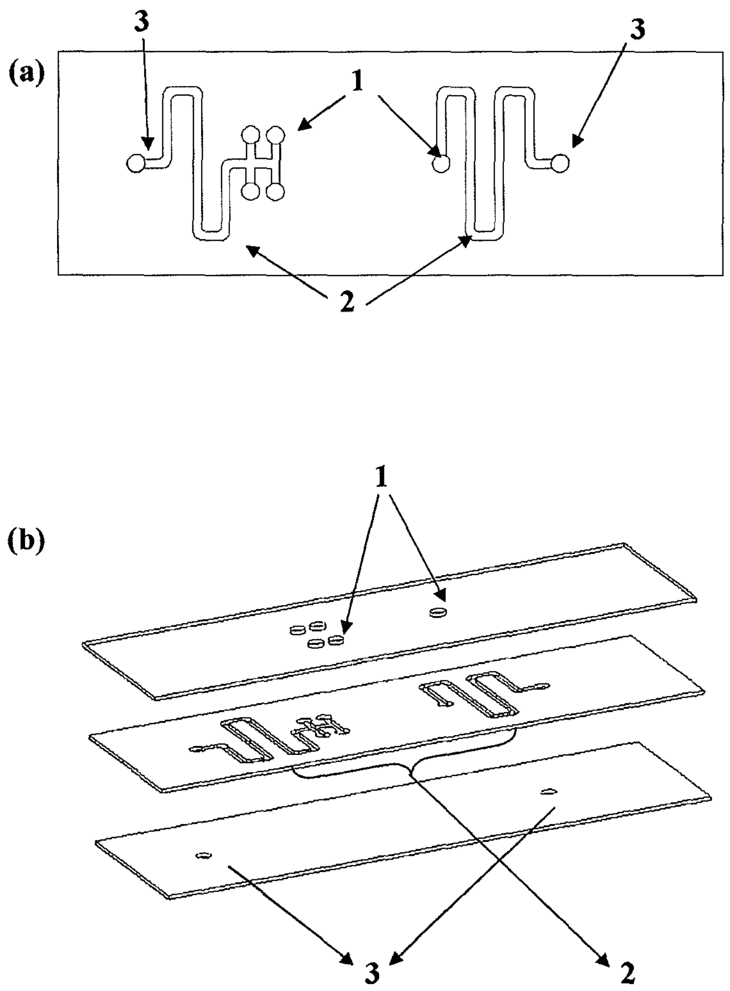
FIG. 1 is the schematic diagram showing the interface device that prevents the contamination between an individual sample and the instrument interfaces.

As illustrated in FIG. 1, the schematic diagram shows the interface device that prevents the contamination between an individual sample and an instrument interface, wherein (a) is a plane schematic diagram and (b) is a three-dimensional structural schematic diagram. 1 is the instrument interface of the interface device, and 2 is the fluid channel, and 3 is the sample interface of the interface device.

Example 2

As illustrated in FIG. 2, the schematic diagram shows the interface device for bio-chip that prevents the cross contamination among a plurality of samples and the contamination between the sample and the instrument interface. 1 is the instrument interface of the interface device; 3 is the sample interface of the interface device; 2-1 is the fluid channel for preventing the cross contamination among a plurality of different samples; 2-2 is the fluid channel for preventing the contamination between the sample and the instrument interface.

Example 3

FIG. 3 is the schematic diagram showing the effect of the interface device for bio-chip described herein for preventing the contamination of the static hybridization bio-chip.

As shown in FIG. 3, the hybridization chip is a kind of common microarray hybridization chip at present, which can be a DNA chip or a protein chip, and is comprised of an enclosed cavity and two sample wells. After adding sample solution into the sample well of the bio-chip, the sample interface of the interface device described herein and the sample well of the bio-chip are connected together and sealed by an adhesive or by clamping using the mechanical clamp, so that the instrument interface of the interface device is closed.

After placing the interface device and the bio-chip into the hybridization box, the contact contamination between the sample solution and the hybridization box can be avoided when static water bath or air bath hybridization is carried out, and the interface device is disposable, so that the cleaning step of the hybridization box can be omitted, and the hybridization experiment of bio-chip can be repeated for many times using the same one hybridization box.

Example 4

FIG. 4 is the schematic diagram showing the effect of the interface device for bio-chip described herein to prevent the contamination of the reversing flow hybridization bio-chip.

In FIG. 4*a*, 1 is the instrument interface of the interface device for bio-chip; 2 is the fluid channel; 3 is the sample interface of the interface device for bio-chip; 4 is the interface device; 5 is the reversing flow hybridization bio-chip, the structural diagram of which is shown in FIG. 4(*d*); wherein 11 is the cover layer; 12 is the microfluid layer; 13 is the microarray chip, which can be a DNA chip or a protein chip, with a size of 25×75 mm; 14 is the through hole; 15 is the microfluid channel; 16 is the hybridization reaction chamber; 17 is the bio-probe array. The material for the microfluid layer is silicon wafer. The microfluid layer is sealed with the microarray chip by an emulsion adhesive to form a plate structure with microfluid channel inside. The hybridization reaction chamber is connected with the bio-probe array of the microarray chip, the shape and area of which corresponds to those of the bio-probe array of the microarray chip.

After adding sample solution into the through hole of the reversing flow hybridization bio-chip, the sample interface of the interface device described herein is connected to the through hole, and the sample interface is sealed with the through hole by adhesive or by clamping using the mechanical clamps. The gas outlet of the pump valve system used to supply reversing flow power is connected to the instrument interface of the interface device, both of which can be closely connected together by a lock ring or a sealing element.

As shown in FIGS. 4*b* and 4*c*, when the pump valve system used to supply gas pressure starts to work, it pushes the sample solution in a manner of positive pressure until the DNA sample reaches the hybridization reaction chamber, and thereafter, it drives the sample solution back in a manner of negative pressure. When moves back and forth in the hybridization reaction chamber, the sample solution flows from the bio-chip in the lower layer to the fluid channel of the interface device in the upper layer through the sample interface. The fluid channel is designed long enough to make sure that the sample solution will not contact the instrument interface during the reversing flow, and thus the contamination problem due to the direct contact between the sample solution and the interface of the pump valve system can be avoided. Since the interface device for bio-chip is a disposable chip, the cleaning step of the catheter or the interface of the pump valve can be avoided, and the chip hybridization experiment can be repeated for many times using the same one pump valve system.

The content described above is only the preferable embodiments of the present invention, and it should be noted that several improvements and modifications can be made by the person of ordinary skill in the art without departing from the principles of the present invention. These improvements and modifications should also be regarded as in the scope of the present invention.

The invention claimed is:

1. An interface device for bio-chip, wherein the interface device comprises at least one interface unit formed by an instrument interface layer, a fluid channel layer and a sample interface layer sealed together, wherein the instrument interface layer is provided with at least one instrument interface, the fluid channel layer is provided with a hollow-out fluid channel, the sample interface layer is provided with at least one sample interface, and the two ends of the fluid channel are connected to the sample interface and the instrument interface, respectively.

2. The interface device according to claim 1, wherein the materials for the instrument interface layer are selected from the group consisting of glass, high molecular polymer, silicon wafer, metal or metal oxide.

3. The interface device according to claim 1, wherein the materials for the fluid channel layer are selected from the group consisting of glass, high molecular polymer, silicon wafer, metal or metal oxide.

4. The interface device according to claim 1, wherein the materials for the sample interface layer are selected from the group consisting of glass, high molecular polymer, silicon wafer, metal or metal oxide.

5. The interface device according to claim 1, wherein the sealing is carried out using an adhesive.

6. The interface device according to claim 5, wherein the adhesive is calendering adhesive, melt adhesive, reactive adhesive, solvent adhesive, emulsion adhesive or solventless liquid adhesive.

7. The interface device according to claim 1, wherein the sealing is carried out by welding.

8. The interface device according to claim 1, wherein the sealing is carried out by placing a sealing element.

9. The interface device according to claim 1, wherein the number of the sample interface is from 1 to 8.

10. The interface device according to claim 1, wherein the number of the instrument interface is from 1 to 8.

* * * * *